(12) United States Patent
Mori

(10) Patent No.: US 7,857,764 B2
(45) Date of Patent: Dec. 28, 2010

(54) MEDICAL IMAGE DIAGNOSTIC APPARATUS AND METHOD OF PERUSING MEDICAL IMAGES

(75) Inventor: Kei Mori, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 529 days.

(21) Appl. No.: 11/224,015

(22) Filed: Sep. 13, 2005

(65) Prior Publication Data

US 2006/0058625 A1    Mar. 16, 2006

(30) Foreign Application Priority Data

Sep. 13, 2004    (JP) .............................. 2004-265713

(51) Int. Cl.
*A61B 8/00* (2006.01)
*G06K 9/00* (2006.01)

(52) U.S. Cl. ......................... 600/437; 382/128; 600/407

(58) Field of Classification Search ................. 600/437, 600/440, 407; 382/128
See application file for complete search history.

(56) References Cited

U.S. PATENT DOCUMENTS

| | | | | |
|---|---|---|---|---|
| 5,920,317 | A * | 7/1999 | McDonald | 715/853 |
| 6,983,064 | B2 * | 1/2006 | Song | 382/131 |
| 2002/0021828 | A1 * | 2/2002 | Papier et al. | 382/128 |
| 2002/0029264 | A1 * | 3/2002 | Ogino et al. | 709/223 |
| 2002/0152401 | A1 * | 10/2002 | Zhang et al. | 713/201 |
| 2003/0023155 | A1 * | 1/2003 | Tsunoda | 600/407 |
| 2003/0095144 | A1 * | 5/2003 | Trevino et al. | 345/764 |
| 2003/0095150 | A1 * | 5/2003 | Trevino et al. | 345/810 |
| 2003/0112922 | A1 * | 6/2003 | Burdette et al. | 378/65 |
| 2004/0068423 | A1 * | 4/2004 | Shaw | 705/3 |
| 2004/0077952 | A1 * | 4/2004 | Rafter et al. | 600/481 |
| 2004/0122702 | A1 * | 6/2004 | Sabol et al. | 705/2 |
| 2004/0267122 | A1 * | 12/2004 | Nadadur et al. | 600/440 |
| 2005/0073578 | A1 * | 4/2005 | Odlivak et al. | 348/65 |
| 2005/0094017 | A1 * | 5/2005 | Hirakawa | 348/333.01 |
| 2005/0114175 | A1 * | 5/2005 | O'Dea et al. | 705/2 |
| 2005/0187472 | A1 * | 8/2005 | Lysyansky et al. | 600/437 |

(Continued)

FOREIGN PATENT DOCUMENTS

AP    2000-189415    7/2000

(Continued)

*Primary Examiner*—Eric F Winakur
*Assistant Examiner*—Helene Bor
(74) *Attorney, Agent, or Firm*—Oblon, Spivak, McClelland, Maier & Neustadt, L.L.P.

(57) ABSTRACT

An ultrasound diagnostic system 200 is provided with operation input device 6 configured to set up examination information of examinee P, operation acknowledgement device 110 configured to acknowledge operation signals received from operation input device 6, operation log discriminator configured to issue time when an operation log ID is acceptable, image information memory 130 configured to store examination image data, index generator configured to read examination image data from image information memory 130 and monitor 5 configured to display the examination image data. Image information memory 130 further stores search information at a predetermined period of time after the time issued by operation log ID discriminator 120 together with examination image data at such a predetermined period of time after the time while index generator 140 reads first examination image data from image information memory 130 and makes monitor 5 display the same.

20 Claims, 11 Drawing Sheets

U.S. PATENT DOCUMENTS

| | | | |
|---|---|---|---|
| 2005/0246388 A1 * | 11/2005 | Yamatake | 707/200 |
| 2006/0085407 A1 * | 4/2006 | Kaminaga et al. | 707/3 |
| 2006/0177114 A1 * | 8/2006 | Tongdee et al. | 382/128 |
| 2007/0019849 A1 * | 1/2007 | Kaufman et al. | 382/128 |
| 2007/0078873 A1 * | 4/2007 | Avinash et al. | 707/101 |
| 2007/0232885 A1 * | 10/2007 | Cook et al. | 600/407 |

FOREIGN PATENT DOCUMENTS

| | | |
|---|---|---|
| JP | 9-51876 | 2/1997 |
| JP | 2001-005902 | 1/2001 |
| JP | 2002-153450 | 5/2002 |

* cited by examiner

| EXAMINATION START TIME | EXAMINEE ID | NAME | NO. OF CHAPTERS | EXAMINATION ITEM |
|---|---|---|---|---|
| 2004/06/22 10:50:13 | 79030310 | Y.T | 3 | ABDOMEN HEART |
| 2004/06/21 11:25:29 | 79030310 | Y.T | 2 | HEART |
| 2004/06/21 10:28:41 | 79030310 | Y.T | 4 | ABDOMEN |
| 2004/06/21 9:30:37 | 12309293 | K.T | 6 | PELVIS |
| 2004/06/21 9:30:35 | 83902314 | T.Z | 1 | ABDOMEN |

FIG. 7

MEDICAL IMAGE DIAGNOSTIC APPARATUS AND METHOD OF PERUSING MEDICAL IMAGES

CROSS-REFERENCE TO RELATED APPLICATION

This application is based upon and claims the benefit of priority from the prior Japanese Patent Application No. 2004-265713, filed on Sep. 13, 2004, the entire contents of which are incorporated herein by reference.

FIELD OF THE INVENTION

This invention generally relates to a medical image diagnostic apparatus and a method of inspecting medical image data and, more particularly, to a medical image diagnostic apparatus configured to store and search image data obtained from an imaging device and a method of perusing such medical image data.

Although descriptions herein are primarily directed to an ultrasound diagnostic apparatus and a method of inspecting medical image data obtained from an ultrasound diagnostic apparatus, they are also applicable to other medical image diagnostic apparatus and methods of perusing medical images.

BACKGROUND OF THE INVENTION

An operator such as an ultrasound examiner or a sonographer carries out a medical inspection for, particularly, circulatory organs of an examinee with an ultrasound diagnostic apparatus. Image data obtained from the ultrasound diagnostic apparatus are recorded on recording media or photographs for medical examinations. An examiner such as a doctor examines the image data reproduced from the recording media or photographs for the medical diagnosis. Such a medical diagnostic operation has been widely practiced.

A video cassette recorder (VCR), for example, is used to record image data obtained from an ultrasound imaging device of an ultrasound diagnostic apparatus on recording media such as magnetic tapes. A doctor searches image date of his or her examinee from recording media collected for each medical inspection and diagnoses illness of the examinee Since in this case, however, the operator taking ultrasound photographs and the examiner are different, unless the examiner is correctly informed of what the operator has taken and photographing timings, the examiner will repeat operations for rapid forwarding, rewinding or the like to locate desired image data from the recoding media for diagnosis, and take additional time unexpectedly.

In order to solve such problems there have been methods proposed for an examiner to conveniently search desired image data in which an examinee ID, name, examination information and the like are transmitted to an examiner together with photographic time information of ultrasound image data and counter data of a VCR and in which address signals are recorded at the beginning of image data (see Japanese Unexamined Patent Publication Tokkaihei 3-289946, for instance).

When, however, an operator forgets taking notes or recording address signals or is involved in other man-made mistakes in the conventional methods, the image data recorded by the VCR cannot be associated with information described in the notes. Further, when a great deal of image data exist, the operator taking ultrasound photographs are very troublesome to take notes or record the address signals.

An object of the present invention is to solve such problems and provide a medical image diagnostic apparatus in which desired image data are easily located and a method of perusing such medical image data.

SUMMARY OF THE INVENTION

A medical image diagnostic apparatus in accordance with an embodiment of the present invention is provided with an operation input device configured to input and set up examination items, a memory to store images formed in response to the examination items set up through the operation input device together with identification information associated to the images, and a monitor configured to display the images of the examination items designated and collected in accordance with the identification information and read out from the memory.

A method of perusing medical images in accordance with the other embodiment of the present invention carries out generating images of an examinee, collecting the images, setting up examination items, adding identification information to the collecting images in accordance with the examination items, storing the images together with the identification information, and displaying the images collected in response to the identification information.

According to the present invention, since search information is stored together with image data in response to examination operations, desired image data are easily located, so that diagnosis efficiency can be remarkably improved.

BRIEF DESCRIPTION OF THE DRAWINGS

A more complete appreciation of the present invention and many of its attendant advantages will be readily obtained as the same becomes better understood by reference to the following detailed descriptions when considered in connection with the accompanying drawings, wherein:

FIG. 7 is an examination list displayed on a monitor screen of the ultrasound diagnostic system in accordance with the first embodiment of the present invention;

DETAILED DESCRIPTION OF THE INVENTION

Figure 1:
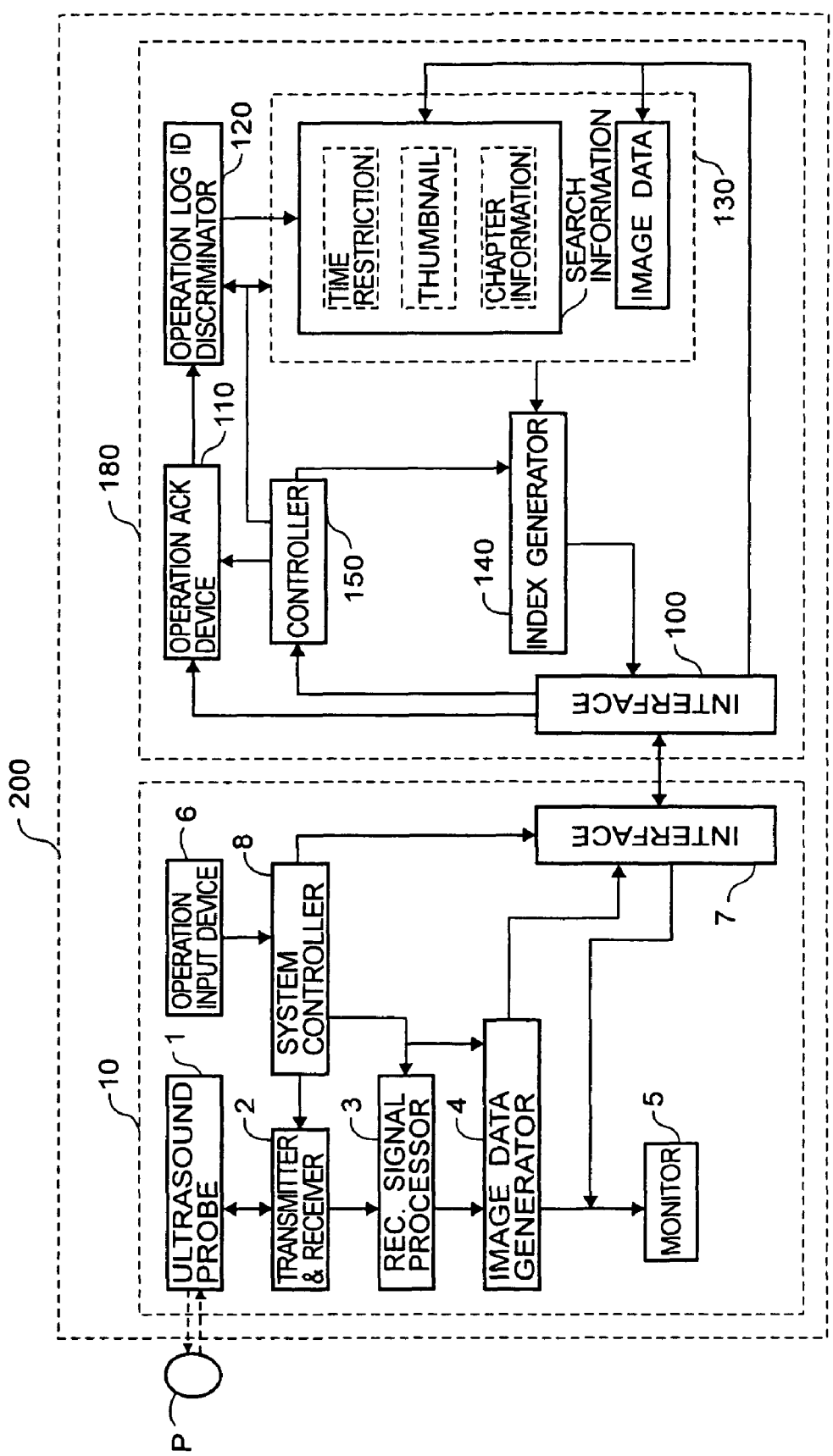
FIG. 1 is an ultrasound diagnostic system in accordance with the first embodiment of the present invention.

Embodiments of the present invention will be explained below with reference to the attached drawings. It should be noted that the present invention is not limited to the embodiments but covers their equivalents. Throughout the attached drawings, similar or same reference numerals show similar, equivalent or same components. The drawings, however, are shown schematically for the purpose of explanation so that their components are not necessarily the same in shape or dimension as actual ones. In other words, concrete shapes or dimensions of the components should be considered as described in these specifications, not in view of the ones shown in the drawings. Further, some components shown in the drawings may be different in dimension or ratio from each other.

First Embodiment

An ultrasound diagnostic system in accordance with the first embodiment of the present invention will be described with reference to FIGS. 1-10.

FIG. 1 is a block diagram of the ultrasound diagnostic system. Ultrasound diagnostic system 200 is provided with ultrasound diagnostic device 10 to take ultrasound pictures of examinee P and image memory and perusal device 180 connected to ultrasound diagnostic device 10 to record (store) and reproduce image data of examinee P supplied from ultrasound diagnostic device 10.

Next, the structure of ultrasound diagnostic device 10 will be explained. Ultrasound diagnostic device 10 is provided with ultrasound probe 1 as a medical image detector and transmitter and receiver 2. Ultrasound probe 1 transmits ultrasound to, and receives the same from, examinee P. Transmitter and receiver 2 supplies drive signals to probe 1, receives reflection signals from probe 1 and processes the reflection signals.

Ultrasound diagnostic device 10 is also provided with receiving signal processor 3, image data generator 4 and monitor 5. Receiving signal processor 3 generates data such as "B" mode data and color Doppler data from the signals processed in transmitter and receiver 2. Image data generator 4 generates image data such as "B" mode image data and color Doppler image data from the data generated by receiving signal processor 3. Monitor 5 displays such image data.

Ultrasound diagnostic device 10 is further provided with operation input device to input information of examinee P and various command signals, interface 7 to communicate with image memory and perusal device 180, and system controller 8 to control the elements in ultrasound diagnostic device 10.

Ultrasound probe 1 is provided with a plurality of linearly disposed piezoelectric elements at its front edge to be in contact with the surface of examinee P to transmit and receive ultrasound. The piezoelectric elements are electric-to-acoustic transducers to transduce electric pulses (driving pulses) into ultrasound pulses during the transmission and transduce reflecting ultrasound (receiving ultrasound) into electric pulses (receiving signals) during the reception.

Since ultrasound probe 1 has various types of scans such as sector scan, linear scan and convex scan, ultrasound probes of those types are connected to transmitter and receiver 2 and one type of ultrasound probe 1 is selected through operation input device 6 to comply with ultrasound photographing requirements.

Transmitter and receiver 2 is provided with an ultrasound transmitter and an ultrasound receiver which are not shown. The ultrasound transmitter generates trigger signals while the ultrasound receiver sums up phased signals received from a plurality of channels of the piezoelectric elements in ultrasound probe 1.

Receiving signal processor 3 processes the resultant phased signals and supplies data such as "B" mode data and color Doppler data to image data generator 4.

Image data generator 4 is provided with a data storage circuit which is not shown but stores the data supplied from receiving signal processor 3. Image data generator 4 reads one or more predetermined phase data from the data storage circuit, processes them, if necessary, and carries out a scan conversion to generate image data such as "B" mode image data and color Doppler image data.

Image data generator 4 also has a function to reduce its generated image data to its reduced image data (thumbnail data). Such image data and thumbnail data are transmitted to image storage and perusal device through interface 7.

Monitor 5 is provided with a color monitor such as a CRT and an LCD panel to display image data supplied from image data generator 4, examination lists and chapter indices such as first and second chapter indices received from image memory and perusal device 180 and image data or the like supplied from image information memory 130.

Operation input device 6 is provided with input devices such as a key board, a track ball, mouse or the like mounted on an operation panel and a display panel. The input devices and the display panel are used to input examinee information such as ID data of examinee P, name and examination items, image data generation modes ("B" mode image data, color Doppler image data, etc.), photographing conditions such as ultrasound scan types, setting data for a moving image recording period of time at moving image storage operations, operations for examination start and end, still image and moving image storage operations, etc.

Various operation signals manipulated with operation input device 6 are transmitted to image memory and perusal device 180 through system controller 8 and interface 7.

System controller 8 is provided with a CPU and a memory circuit not shown in the drawings. The CPU controls transmitter and receiver 2, receiving signal processor 3, image data generator 4, monitor 5 and interface 7 in response to examination information supplied from operation input device 6. The memory of system controller 8 stores examination information such as information of examinee P, photographing conditions and moving image recording period of time.

Next, the structure of image memory and perusal device 180 will be explained. Image memory and perusal device 180 is provided with interface 100, operation acknowledgement device 110 and operation log ID discriminator 120. Interface 100 is used to transmit signals to, and receive the same from, ultrasound diagnostic device 10. Operation acknowledgement device 110 acknowledges an operation signal supplied from operation input device 6, converts the same into an operation log ID and adds receipt time to the ID. Operation log ID discriminator 120 discriminates the operation log ID from operation acknowledgement device 110 and issues time information (distinctive time information) after a predetermined period of time from acknowledgement time of a proper operation log ID. The time information may be other forms of information such as frame ID information which specifies a frame number of image data (multiple frames of moving pictures) corresponding to the time information.

Image memory and perusal device 180 is provided with image information memory 130, index generator 140 and controller 150. Image information memory 130 stores receiving signals from ultrasound diagnostic device 10 through interface 100, such as image data, thumbnail data, examination information, still images and moving-image storage-operation-time information, and distinctive time information, etc., from operation log ID discriminator 120. Index generator 140 reads search information such as first and second search information based on the distinctive time information, still images and moving-image storage-operation time information to generate chapter indices. Controller 150 controls the elements of image memory and perusal device 180.

Operation acknowledgement device 110 receives examination item setting-up operations from operation input device 6 of ultrasound diagnostic device 10, operation signals in response to ultrasound probe setting-up operations and image data generation mode setting-up operations, converts each operation signal into an operation log ID, and supplies the same to operation log ID discriminator 120 after adding receipt time to the operation log ID.

Operation log ID discriminator 120 is provided to discriminate an operation log ID from operation acknowledgement device 110 and issues distinctive time information to image information memory 130 in the case that the operation log ID is in conformity with a predetermined set-up distinctive operation log ID. The distinctive time information may be represented by information of time after a period of time "t" from the acknowledgement of the operation log ID or its equivalent information such as frame ID information.

Image information memory 130 is provided with a recording media such as DVD equipment to store image data generated in image data generator 4 in response to recording start operation signal from operation input device 6.

Image information memory 130 provides the image data with examination information stored in system controller 8, thumbnail data of the image data (recording start thumbnail data) generated in image data generator and first search information (recording start search information) including distinctive time (recording start time) based on the recording start operation signal in accordance with recording start operation signal. The distinctive time may be represented by other equivalent information such as frame ID information at the recording start time.

In order to store image data at the time when operation log discriminator 120 issues distinctive time information based on the discrimination of log ID after starting the record, image information memory 130 adds image data generated in image data generator 4 at the time to thumbnail data (distinctive thumbnail data) generated in image data generator 4 at the time, examination information stored in the memory circuit of system controller 8 at the time, and first search information (distinctive search information) and stores the image data to which the same are added.

Finally, image information memory 130 finishes storing recording image data (examination image data) generated in image data generator at the recoding end in response to a recording end operation signal from operation input device 6, adds the same to incidental information, i.e., examination information at the memory circuit of system controller 8 and thumbnail data from image data generator 4 at the recording end, and stores the recording image data together with such incidental information.

Examination data from image data generator 4 are sorted between the recoding start time and the time specified by the first distinctive time information, the time specified by distinctive time information and that specified by its neighboring distinctive time information, and the time of the last distinctive time information and the recording end time, respectively. Image data generator 4 adds such sorted image data (distinctive image data) to incidental information corresponding thereto, i.e., recording start search information or distinctive search information and stores the sorted image data together with the incidental information. Thus, an examiner can easily search image data later on.

Index generator 140 reads examination information of each of examination image data stored in image information memory 130 and makes up an examination list corresponding to each of examination image data. Further, index generator 140 reads recording start search information and first search information of distinctive search information from each of examination image data stored in image information memory 130, and makes up the first chapter from the first search information and the first chapter index disposing each first chapter in a predetermined order.

Index generator 140 reads the second search information from each examination image data stored in image information memory 130, and makes up the second chapter from each second search information and the second chapter index disposing each second chapter in a predetermined order. Index generator 140 then sends the first and second chapter indices to ultrasound diagnostic device 10 though interfaces 100 and 7.

Index generator 140 also reads examination image data and distinctive image data from image information memory 130 in response to reproduction operation signals from operation input device and transmits the same to monitor 5 of ultrasound diagnostic device 10 through interfaces 100 and 7.

Controller 150 controls interface 100, operation acknowledgement device 110, operation log ID discriminator 120, image information memory 130, index generator 140, etc. in response to control signals supplied from system controller 8 to image memory and perusal device 180.

Figure 2:
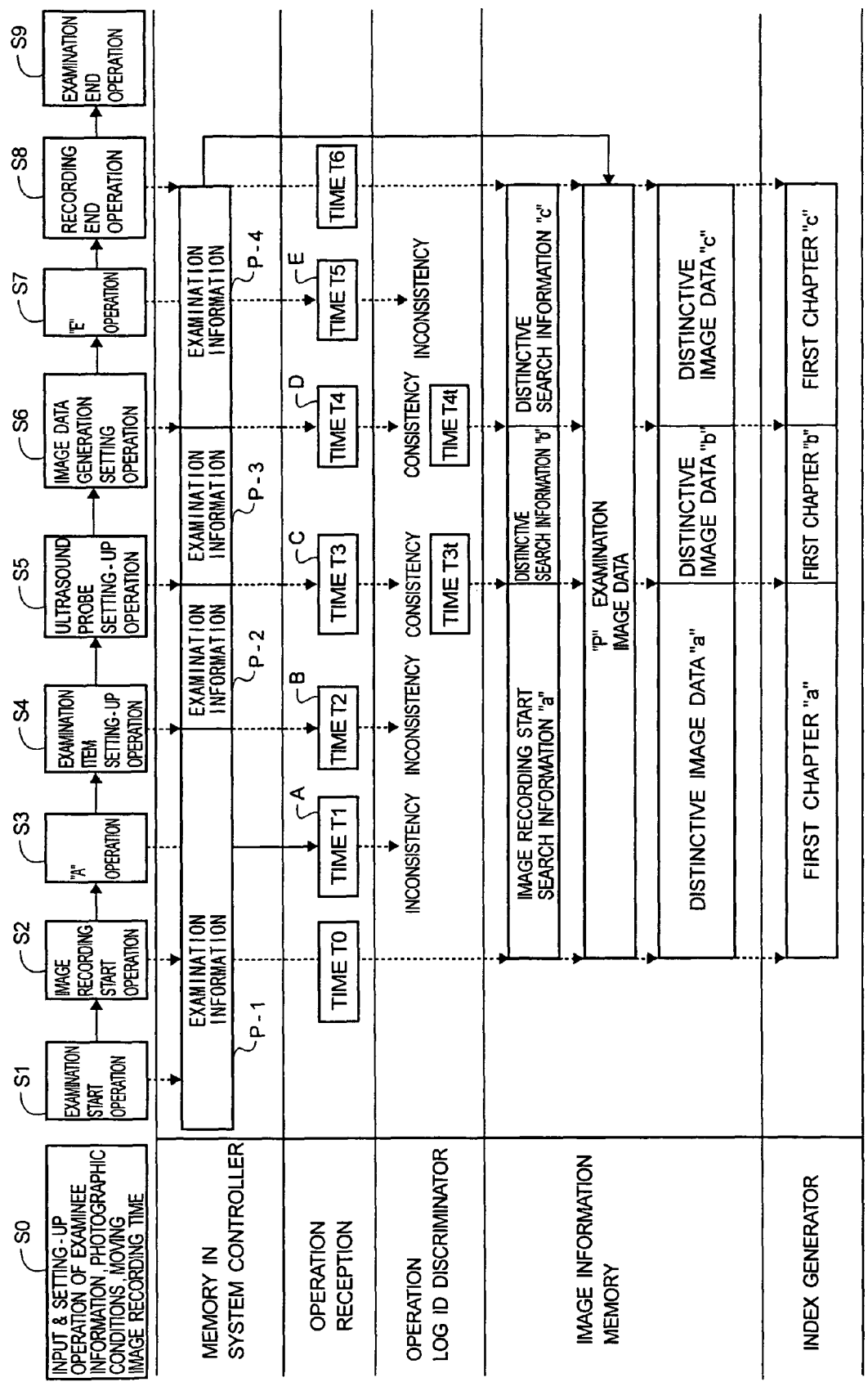
FIG. 2 is a schematic diagram to explain the process and operations of the ultrasound diagnostic system in accordance with the first embodiment of the present invention.

Operations of ultrasound diagnostic system 200 of the first embodiment will be described with reference to FIGS. 1-10. FIG. 2 is a flow chart of ultrasound photographing operation steps in the examination and associated operations of ultrasound diagnostic system 200.

After an operator connects sector scan, linear scan and/or convex scan type ultrasound probe 1 to ultrasound diagnostic system 200, he or she turns on ultrasound diagnostic system 200. The operator inputs an instruction of a display operation through operation input device 6 and sets up distinctive operations while viewing a distinctive operation setting-up screen on monitor 5 in response to the display operation.

Figure 3:
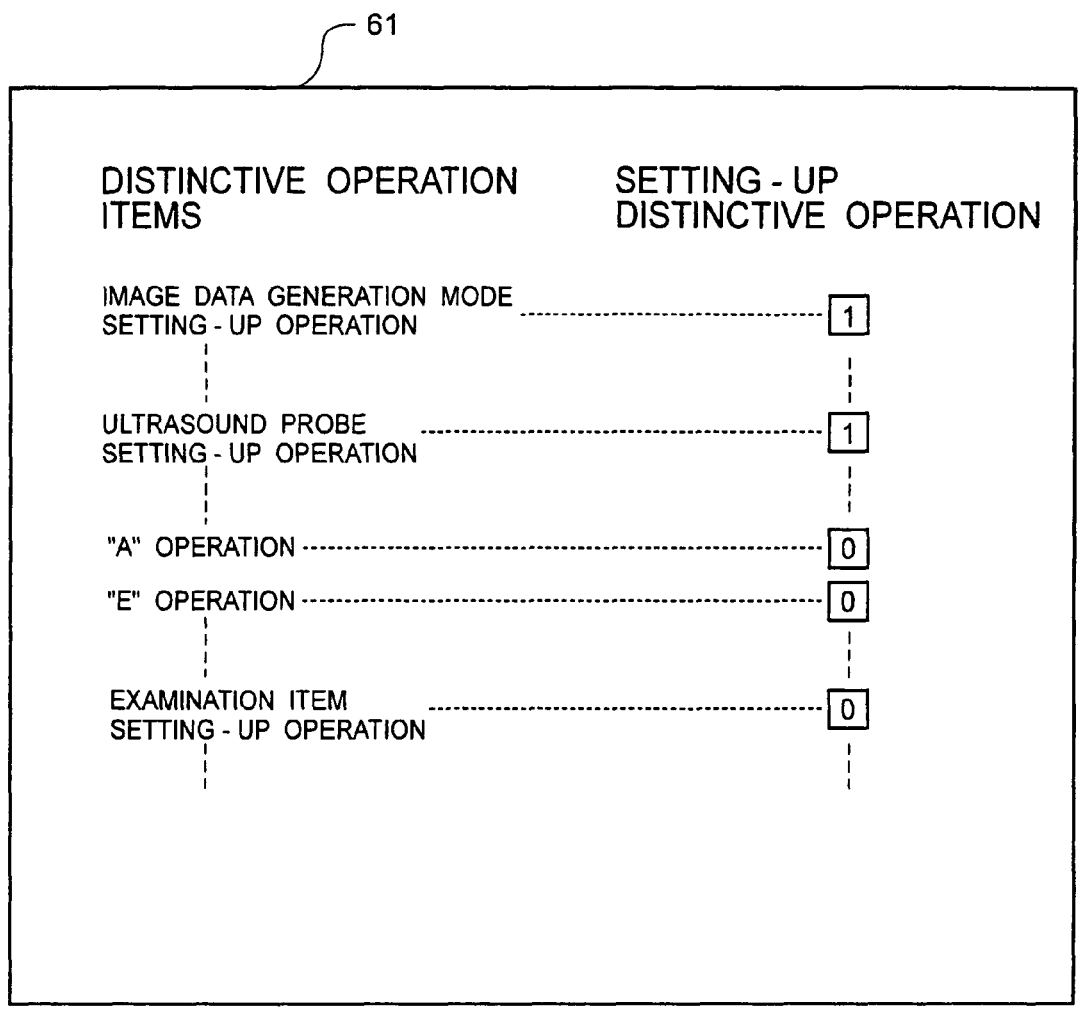
FIG. 3 is an example of distinctive operation setting-up items displayed on a monitor screen of the ultrasound diagnostic system in accordance with the first embodiment of the present invention.

FIG. 3 shows one example of such a distinctive operation setting-up screen. Distinctive operation setting-up screen 61 has columns of "distinctive operation items" and "setting-up distinctive operations".

The column of "distinctive operation items" includes various items of operations (log ID) in response to operation input device 6 such as "image data generation mode setting-up operation", "ultrasound probe selection setting-up operation", "A operation", "E operation", "examination item setting-up operation" or the like.

Further, input square frames are provided for columns of "image data generation mode setting-up operations", "ultrasound probe type setting-up operations" or the like corresponding to each distinctive operation item and "1" or "0" can be set at the square frame. In the case that "1" is set at a square frame, an operation signal is applied as a timing signal for examination image data to be stored in image information memory 130 at the time when corresponding "distinctive operation items" are designated with operation input device 6 but no operation signal is applied in the case that "0" is set at a square frame.

As described above, since operation items useful for image data search information can be set by viewing distinctive data setting-up screen 61, whenever operations required for examinations are designated through operation input device 6, examination information is sorted at that time and stored in image information memory 130.

Operations will be described below on the assumption here that "1" is set at square frames of "image data generation mode setting-up operations" and "ultrasound probe type setting-up operations" while "0" is set at square frames of "A operations", "E operations", . . . and "examination item setting-up operations".

Operation inputs are provided through operation input device 6 to set up information of examinee P and examination information such as photographing conditions and the like. With respect to examination items of examinee information, standard photographing conditions for each diagnostic portion are set up in advance by the manipulation of preset operation buttons of operation input device 6 provided for examination items.

It is also assumed that examinee ID of "79030310", examinee's name of "Y.T", examination portion of "abdomen", image data generation mode of "B mode image data", ultrasound probe type of "convex scan" and moving image recording time of "5 seconds" have been input or selectively set up (Step S0 in FIG. 2).

Next, examination information P-1 composed of examination information of examinee P and examination start time (for example, "2004/06/22 10:50:13") is stored in the memory circuit in system controller 8 in response to an examination start operation signal from operation input device 6 (Step S1 in FIG. 2).

When ultrasound probe 1 is put in contact with the abdomen of examinee P for ultrasound photographing, "B" mode image data are generated in image data generator 4 from image data sent through transmitter and receiver 2 and receiving signal processor 3 and the same are displayed on a real time basis on monitor 5. In response to recording start operation signals at time T0 from operation input device 6 image information memory 130 starts storing image data of examinee P generated in image data generator 4 (Step S2 in FIG. 2). Controller 150 adds "B" mode P examination image data generated at time T0 in image data generator 4 to recording start search information "a" at time T0 composed of recording start thumbnail data at time T0 and examination information P-1 at time T0 and image information memory 130 stores such added image data.

Figure 4:
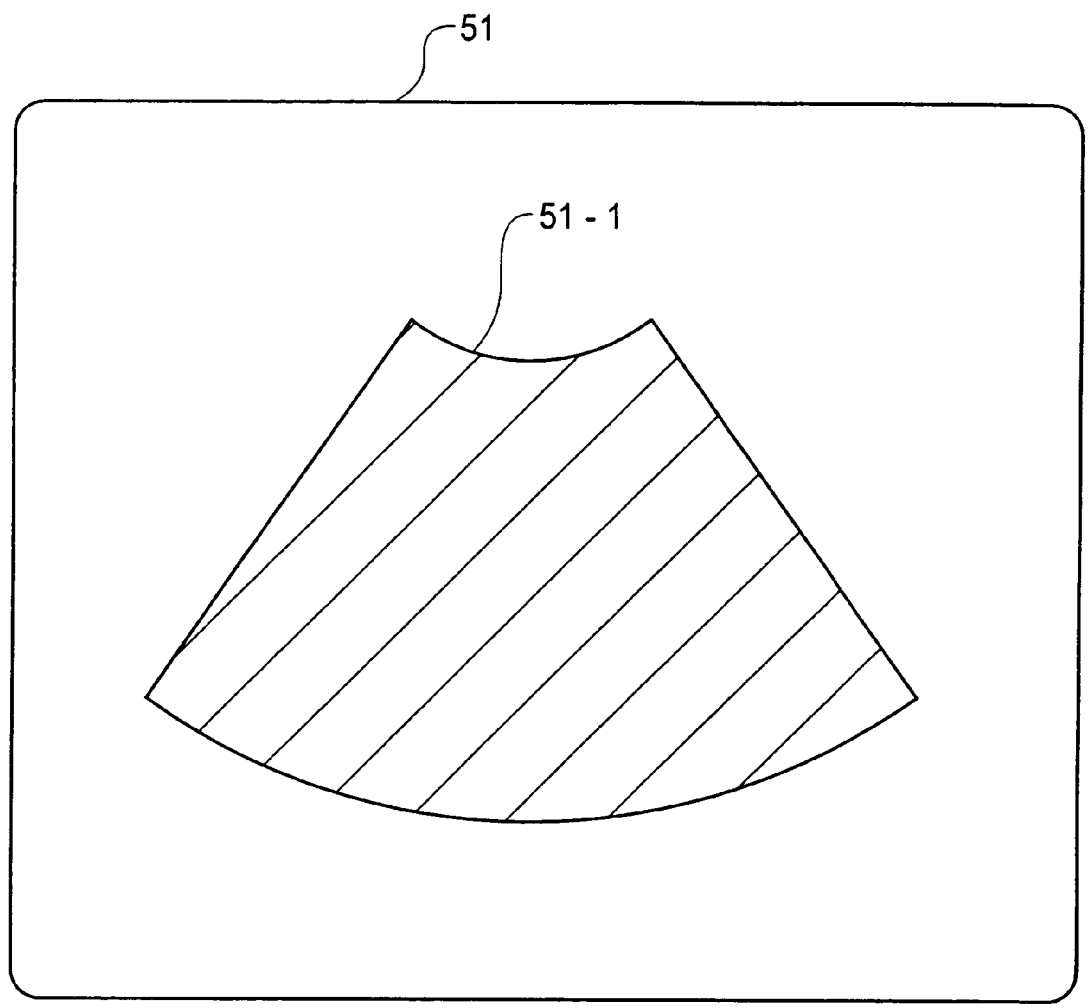
FIG. 4 is a diagnostic image displayed on a monitor screen of the ultrasound diagnostic system in accordance with the first embodiment of the present invention.

FIG. 4 shows an example of an image displayed on monitor 5 just after recording start operations through operation input device 6. The image displayed on screen 51 of monitor 5 is "B" mode image 51-1 corresponding to "B" mode image data of the abdomen of examinee P generated in image data generator 4 just after such recording start operations. Thumbnail data of the "B" mode image data are consistent to recording start thumbnail data.

Next, when an "A" operation is instructed through operation input device (Step S3 in FIG. 2), operation acknowledgement device 110 receives the "A" operation and converts the same into an "A" operation log ID. Operation acknowledgement device 110 then adds reception time T1 to the "A" operation log ID to form information "A" and outputs the same to operation log ID discriminator 120. In order to discriminate the information "A" operation log ID discriminator 120 collates the same with distinctive operation log ID set up in advance on distinctive operation setting-up screen 61 shown in FIG. 3. In the case of an example shown in FIG. 3, since the "A" operation has not been set up as a distinctive operation, operation log ID discriminator 120 discriminates that the same is inconsistent so that time T1 of information "A" is not inputted to image information memory 130. Since examination information corresponding to an operation "A" is also not included, examination information P-1 remains unchanged.

Next, the operator moves ultrasound probe 1 to the breast of examinee P to change the diagnostic portion to the heart, for example, and manipulates examination item pre-set buttons of operation input device 6 to input an instruction of examination item setting-up operations for the heart.

In response to examination item setting-up signals (Step S4 in FIG. 2), the memory circuit of system controller 8 stores examination information P-2 composed of examination information P-1 and changing information and time as to examination items which are added to examination information P-1.

Operation acknowledgement device 110 receives the examination item setting-up signal from operation input device 6, converts the same into the operation log ID, and supplies operation log ID discriminator 120 with information "B" composed of the operation log ID and receipt time T2 added. Operation log ID discriminator 120 also compares information "B" from operation acknowledgement device 110 with the distinctive operation log ID set up on operation setting screen 61. Since the "examination item setting-up operation" shown in an example of FIG. 3 is not set up as a distinctive operation, operation log ID discriminator 120 finds the same to be improper so that time T2 of information "B" is not sent to image information memory 130.

Next, the operator alternatively holds sector scan type ultrasound probe 1 and carries out an ultrasound probe selection operation through operation input device 6 to change the use of ultrasound probe 1 to a sector scan type use.

In response to the ultrasound probe selection changing operation signal (Step S5 in FIG. 2), the inner memory circuit of system controller 8 stores examination information P-3 composed of examination information P-2 and changing information and time as to ultrasound probe 1.

Operation acknowledgement device 110 receives the ultrasound probe selection setting-up operation signal from operation input device 6, converts the same into its operation log ID, and supplies operation log ID discriminator 120 with information "C" composed of the operation log ID and receipt time T3 added thereto. Operation log ID discriminator 120 also compares information "C" from operation acknowledgement device 110 with the distinctive operation log ID set up on operation setting screen 61. Since the "examination item setting-up operation" shown in the example of FIG. 3 is set up as a distinctive operation, operation log ID discriminator 120 finds the same to be proper so that time T3$t$ after time "t" from time T3 of information "C" is sent to image information memory 130 as a distinctive time information.

Under control of controller 150 image information memory 130 stores P examination data of "B" mode image data generated at time T3$t$ in image data generator 4 and distinctive search information "b" added thereto and composed of thumbnail data generated at time T3$t$ in image data generator 4, examination information P-3 stored at time T3$t$ in the inner memory circuit of system controller 8 and time T3$t$ Distinctive image data "a" distinguished by recording start time T0 and time T3 is formed in P examination image data of image information memory 130.

In the case that operation signals through operation input device 6 are ultrasound probe selection change operation signals or the like, for example, it takes a certain period of time to change operations at transmitter and receiver 2, receiving signal processor 3 and image data generator 4. Thus, when operation log ID discriminator 120 judges an operation log ID to be proper immediately after an input timing of such change operation, correct image data after the change operation cannot be generated in image data generator 4 or thumbnail data do not become clear enough so that valid thumbnail data cannot be generated either.

To avoid such inconvenient operations, clear thumbnail data are generated in image data generator 4 based on the distinctive operation signal at the time "t" after operation log ID discriminator 120 has found the operation log ID to be proper.

Figure 5:
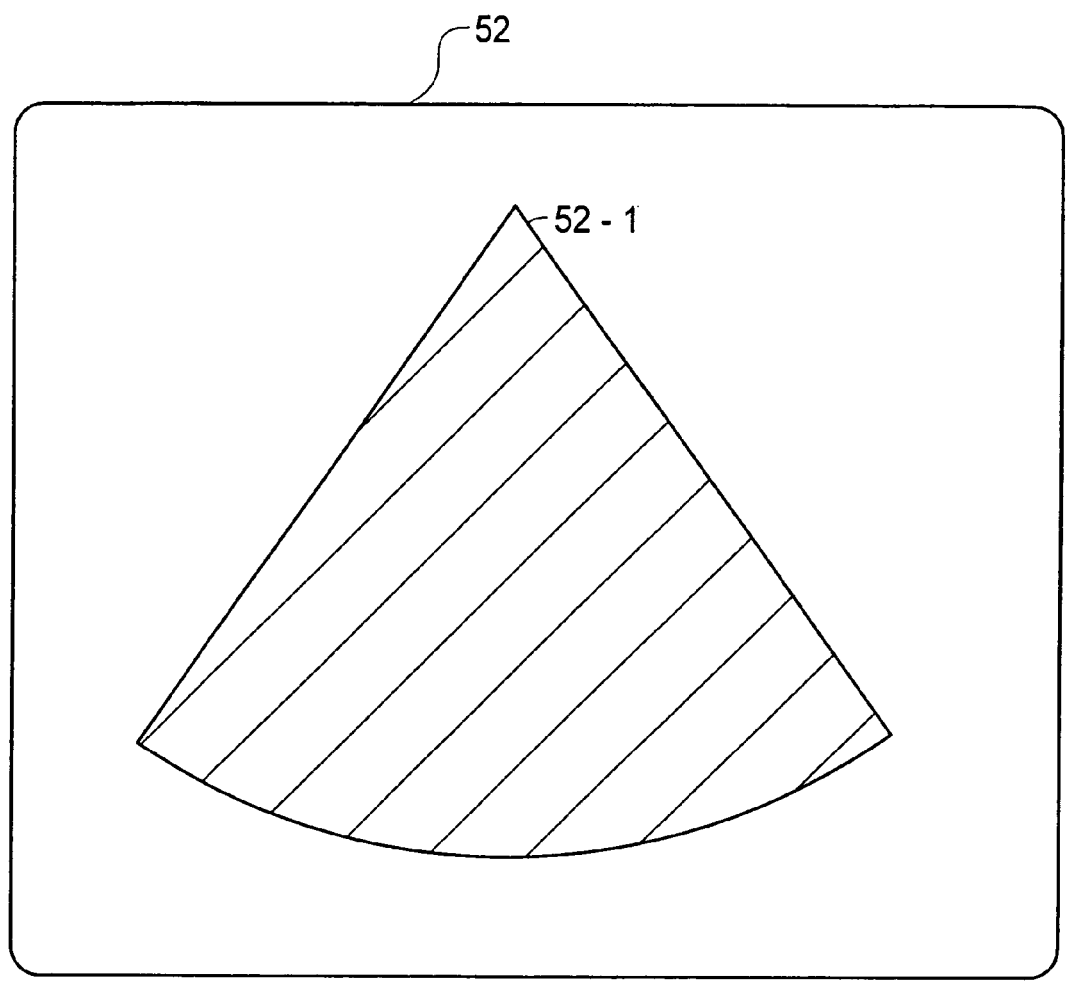
FIG. 5 is another diagnostic image displayed on a monitor screen of the ultrasound diagnostic system in accordance with the first embodiment of the present invention.

FIG. 5 is an example of an image displayed on monitor 5 at time T3t. "B" mode image 52-1 is displayed on screen 52 corresponding to "B" mode image data in the heart of examinee P generated in image data generator 4 at time T3t. Thumbnail data of the "B" mode image data are consistent with the distinctive thumbnail data at time T3t.

Next, it is assumed that the operator changes the operation from the image data generation mode to the color Doppler image data through operation input device 6 to obtain blood flow information at the heart of examinee P, for instance.

In response to the image data generation setting operation signal through operation input device 6 (Step S6 in FIG. 2), the inner memory circuit of system controller 8 stores examination information P-4 composed of examination information P-3 and changing information and time of image data generation mode examination information added thereto.

Operation acknowledgement device 110 receives the image data generation mode setting-up operation signal from operation input device 6, converts the same into its operation log ID, and supplies operation log ID discriminator 120 with information "D" composed of the operation log ID and receipt time T4 added thereto. Operation log ID discriminator 120 compares information "D" from operation acknowledgement device 110 with the distinctive operation log ID set up on operation setting screen 61. Since the "image data generation mode setting-up operation" shown in the example of FIG. 3 is set up as a distinctive operation, operation log ID discriminator 120 finds the same to be proper so that time T4t after time "t" from time T4 of information "D" is sent to image information memory 130 as a distinctive time information.

Under control of controller 150 image information memory 130 stores P examination data of color Doppler image data generated at time T4t in image data generator 4 and distinctive search information "c" added thereto and composed of thumbnail data generated at time T4t in image data generator 4, examination information P-4 stored at time T4t in the inner memory circuit of system controller 8 and time T4t.

Distinctive image data "b" distinguished by recording start time T3t and time T4t is formed in P examination image data of image information memory 130.

Figure 6:
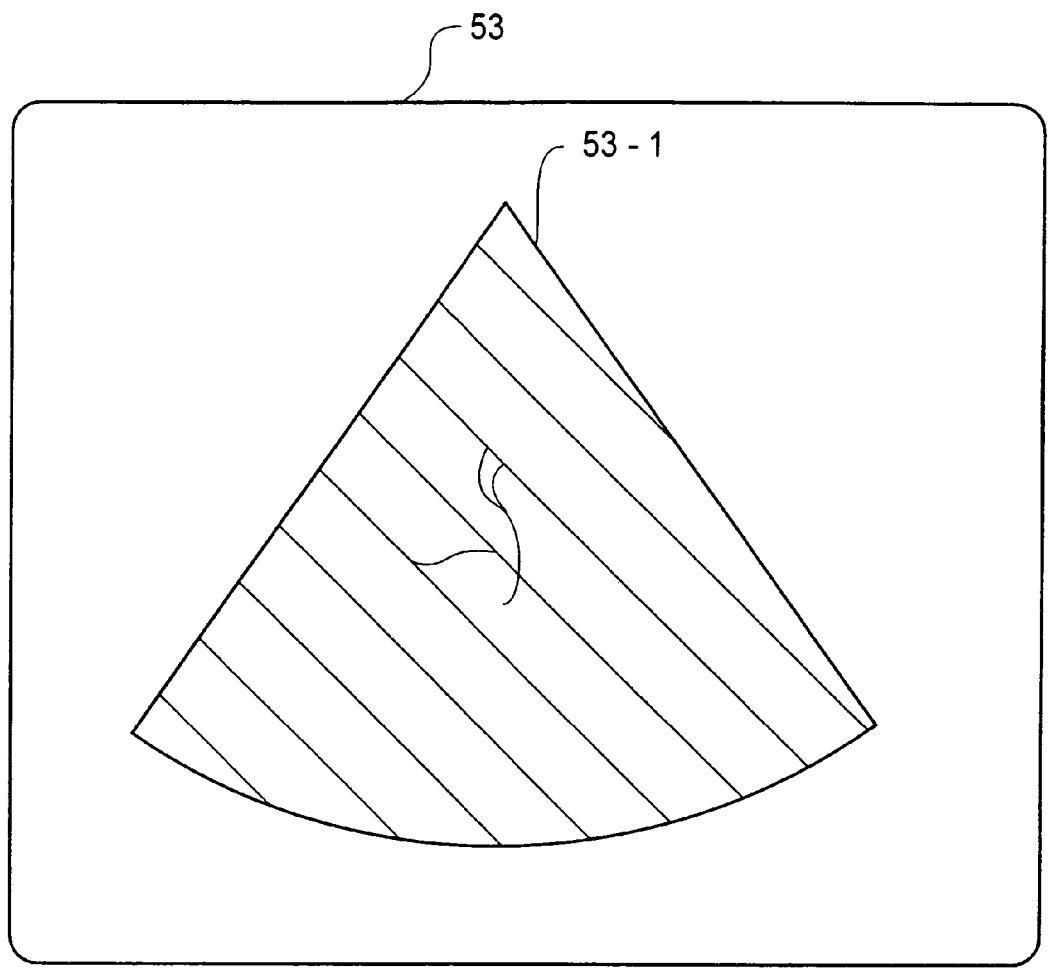
FIG. 6 is a color Doppler diagnostic image displayed on a monitor screen of the ultrasound diagnostic system in accordance with the first embodiment of the present invention.

FIG. 6 is an example of an image displayed on monitor 5 at time T4t. Color Doppler image 53-1 is displayed on screen 53 corresponding to color Doppler image data in the heart of examinee P generated in image data generator 4 at time T3t. Thumbnail data of the color Doppler image data are consistent with the distinctive thumbnail data at time T4t.

Next, in response to the "E operation" (Step S7 in FIG. 2), operation acknowledgement device 11 and operation log ID discriminator 120 carry out the same operation as the "A operation". Since no examination information corresponding to the "E operation" is included, examination information P-4 remains unchanged.

Next, it is further assumed that the operator carries out a recording end operation to finish up recording of P examination of examinee P.

In response to a recording end operation signal through operation input device (Step S8 in FIG. 2), under control of controller 150 image information memory 130 stores P examination image data generated in image data generator at the recording end time and finishes up recording. Image information memory 130 stores the P examination image data, and examination information P-4 stored in system controller 8 and the recording end time added thereto.

Distinctive image data "c" distinguished by recording start time T4t and the recording end time is formed in P examination image data of image information memory 130.

Next, it is further assumed that the operator inputs an examination end signal to the operation input device 6 to finish the examination of examinee P. In response to the examination end signal through operation input device 6 (Step S9 in FIG. 2), system controller 8 stops operations of transmitter and receiver 2 and the like. The ultrasound photographing is finished.

After P examination of examinee P is finished by the operator, a medical examination is conducted by such medical examiners as doctors with reference to P examination image data stored at each step of FIG. 2 at image information memory 130. In this case, first, responding to an examination list display operation and an instruction supplied from operation input device 6 and system controller 8, respectively, controller 150 makes up an examination list from examination image data stored at image information memory 130 while monitor 5 displays the same.

FIG. 7 is an example of the examination list displayed on monitor 5. Controller 150 reads examination information such as "examination start time", "examinee ID", "name", "the number of chapters" and "examination items" for each examination stored in image information memory and such examination information is displayed on examination list screen 54.

Next, when examination information 54-1 corresponding to P examination of examinee P, for instance, is selected from examination list screen 51 of monitor 5 in response to a selection operation through operation input device 6 and its first chapter index display operation is carried out, index generator 140 reads first search information (i.e., recording start search information "a" and distinctive search information "b" and "c") added to P examination image data of image information memory 130 following control instructions of controller 8 supplied through interfaces 7 and 100 and controller 150 and makes first chapters "a", "b" and "c" based on each first search information.

Further, index generator 140 disposes first chapters "a", "b" and "c" in time sequence, makes a first chapter index and sends the same to monitor 5. As a result, the first chapter index is displayed on monitor 5.

Figure 8:
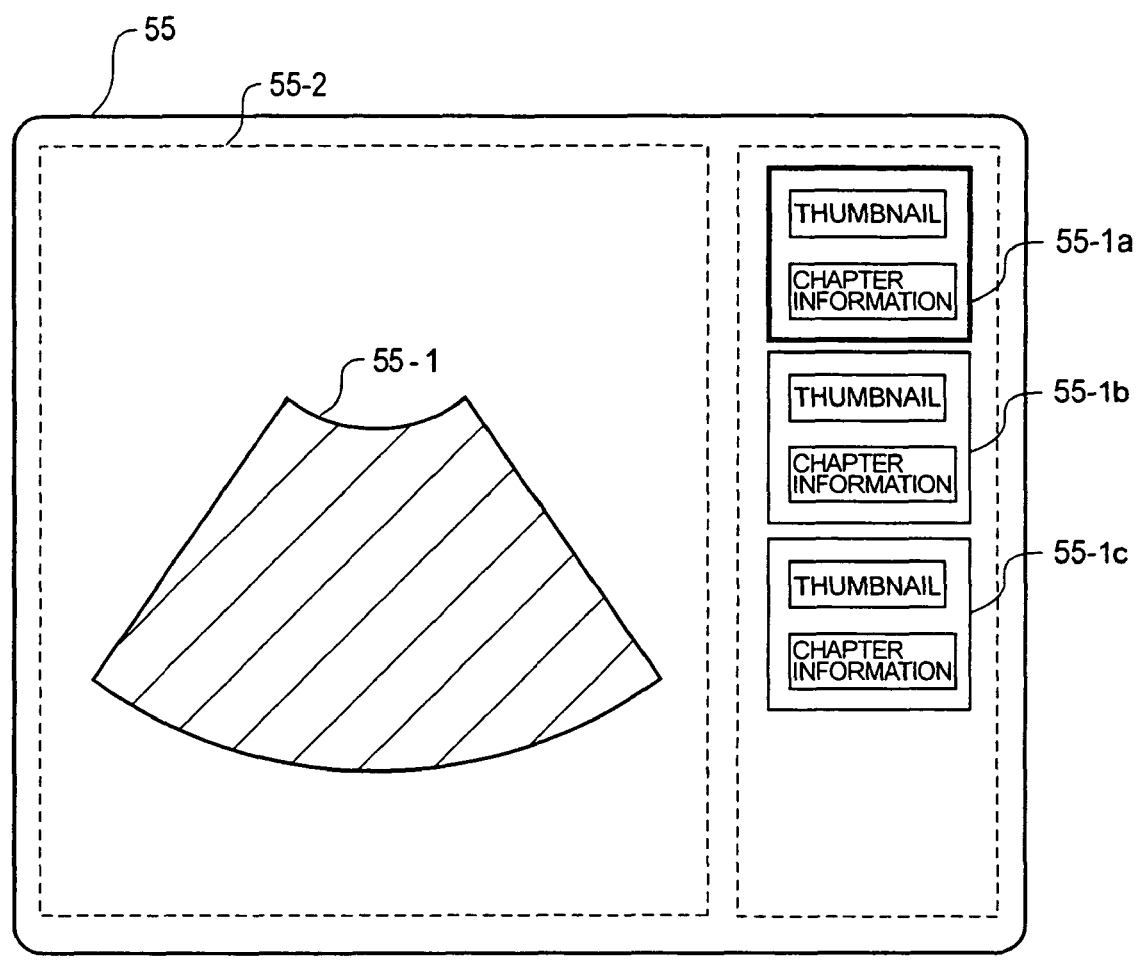
FIG. 8 is the first chapter index displayed on a monitor screen of the ultrasound diagnostic system in accordance with the first embodiment of the present invention.

FIG. 8 is an example of the first chapter index displayed on a screen of monitor 5. First chapter index screen 55 is provided with chapter display area 55-1 to display the first chapter and image display area 55-2 to reproduce and display image data corresponding to the first chapter.

In the case that the first chapter made up by index generator 140 has a plurality of image data in chapter display area 55-1, such image data are disposed and displayed in predetermined order. It is assumed that examination information 54-1, for example, is selected from examination list screen 54 and first chapters "a", "b" and "c" are searched. Index generator 140 disposes the first chapter "a" (55-1a) of the earliest time information at the top and the first chapter "b" and "c" (55-1b and 55-1c) of later and the latest distinctive time information at the lower and lowest places underneath the top, respectively. Further, when the chapter "a" of the top earliest distinctive time information, for example, is selected for highlight display, its "B" mode image data "a" is displayed in image display area 55-2.

Figure 9:
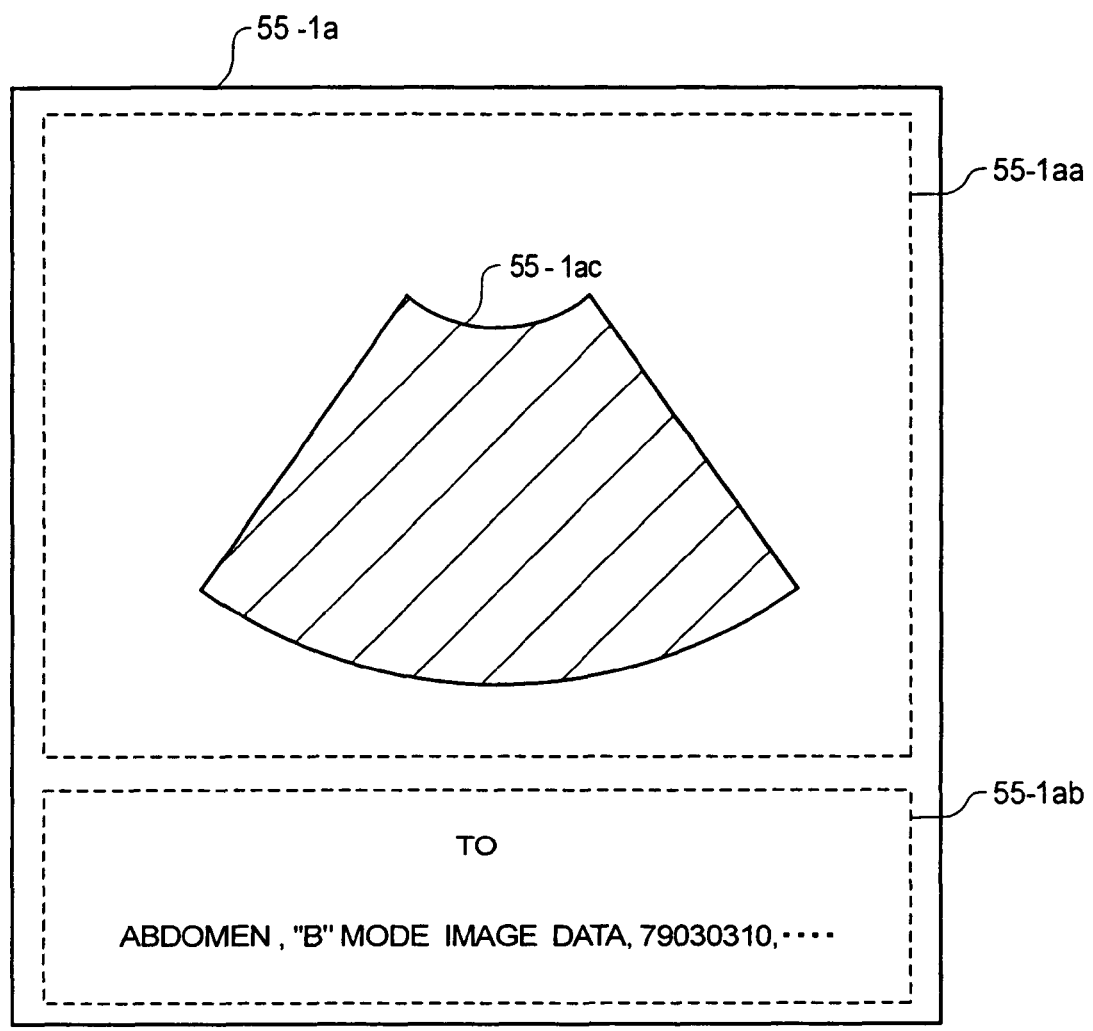
FIG. 9 is the first chapter displayed on a monitor screen of the ultrasound diagnostic system in accordance with the first embodiment of the present invention.

FIG. 9 is an enlarged indication of first chapter "a" (55-1a) displayed in chapter display area 55-1. First chapter "a" (55-1a) is composed of thumbnail display area 55-1aa to display thumbnail data searched in accordance with the first search information and chapter information display area 55-1ab to display that chapter information. Other chapters "b" (55-1b) and "c" (55-1c) are likewise displayed.

In an example of FIG. 9, thumbnail 55-1ac corresponding to thumbnail data (recording start thumbnail data) of the first chapter "a" (55-1a) searched in accordance with examination information 54-1 of FIG. 7 is displayed in thumbnail display area 55-1aa while its enlarged image is "B" mode image 51-1 of FIG. 8. In chapter information display area 55-1ab, recording start time "T0" in recording start search information "a" including thumbnail data, an examination item of "abdomen", an image data generation mode of "'B' mode image data", and examinee ID of "79030310", etc. are displayed as the first chapter information in response to operations instructed in advance through operation input device 6.

When the first chapter cannot be fully displayed on chapter display area 55-1 of FIG. 8, a first chapter can be moved up or down in response to scroll operations instructed through operation input device 6.

If the first chapter in chapter display area 55-1 is displayed in order of time when distinctive time information has occurred, for example, distinctive time information with latest time of the first chapter is displayed from the top. In this case, the distinctive time information with the latest time of the first chapter is highlighted. This highlight display can be moved to any desired first chapter in response to a highlight display moving operation provided through operation input device 6.

When a moving picture reproduction operation provided through operation input device 6 is carried out for "B" mode image 51-1 of image display area 55-2, index generator 140 reproduces and displays image data 51-1 from image information memory 130 at a predetermined reproduction rate. The reproduction rate is adjustable in response to an operation provided through operation input device 6.

When a moving image loop reproduction operation is instructed through operation input device 6, index generator 140 reproduces image data 51-1 from image information memory 130 at the reproduction rate in a disposing order set up in advance. In the case of the example of FIG. 8, distinctive image data "b" of highlighted first chapter "a" (55-1a) are reproduced and displayed in image display area 55-2. Distinctive image data "b" and "c" corresponding to first chapter "b" (55-1b) and "c" (55-1c) are then sequentially reproduced and displayed in image display area 55-2, respectively. When one loop display of the first chapter is completed, the reproduction operation in accordance with the moving image loop reproduction operation is finished.

Further, when examination information 54-1 is selected from examination list screen 61 of monitor 5 in response to a selection operation provided through operation input device 6 and an all image data reproduction operation is carried out, index generator 140 reads P examination image data from image information memory 130 and reproduces and displays the same on image display area 55-2.

First chapter index screen 55 is not limited to chapter display area 55-1 or image display area 55-2. For example, only chapter display area 55-1 may be provided in first chapter index screen 55 to display the first chapter so that selected image data can be alternatively displayed on first chapter index screen 55 in the case of the selection of the first chapter from chapter display area 55-1.

Next, when examination information 54-1 is selected from examination list screen 54 in response to a selection operation provided through operation input device 6 and the second chapter index display is carried out, index generator 140 reads the second search information incidental to P examination image data from image information memory 130 and makes up the second chapter. Further, index generator 140 disposes the second chapter in a predetermined order, forms the second chapter index and sends the same to monitor 5. Monitor 5 displays the second chapter index.

Figure 10:
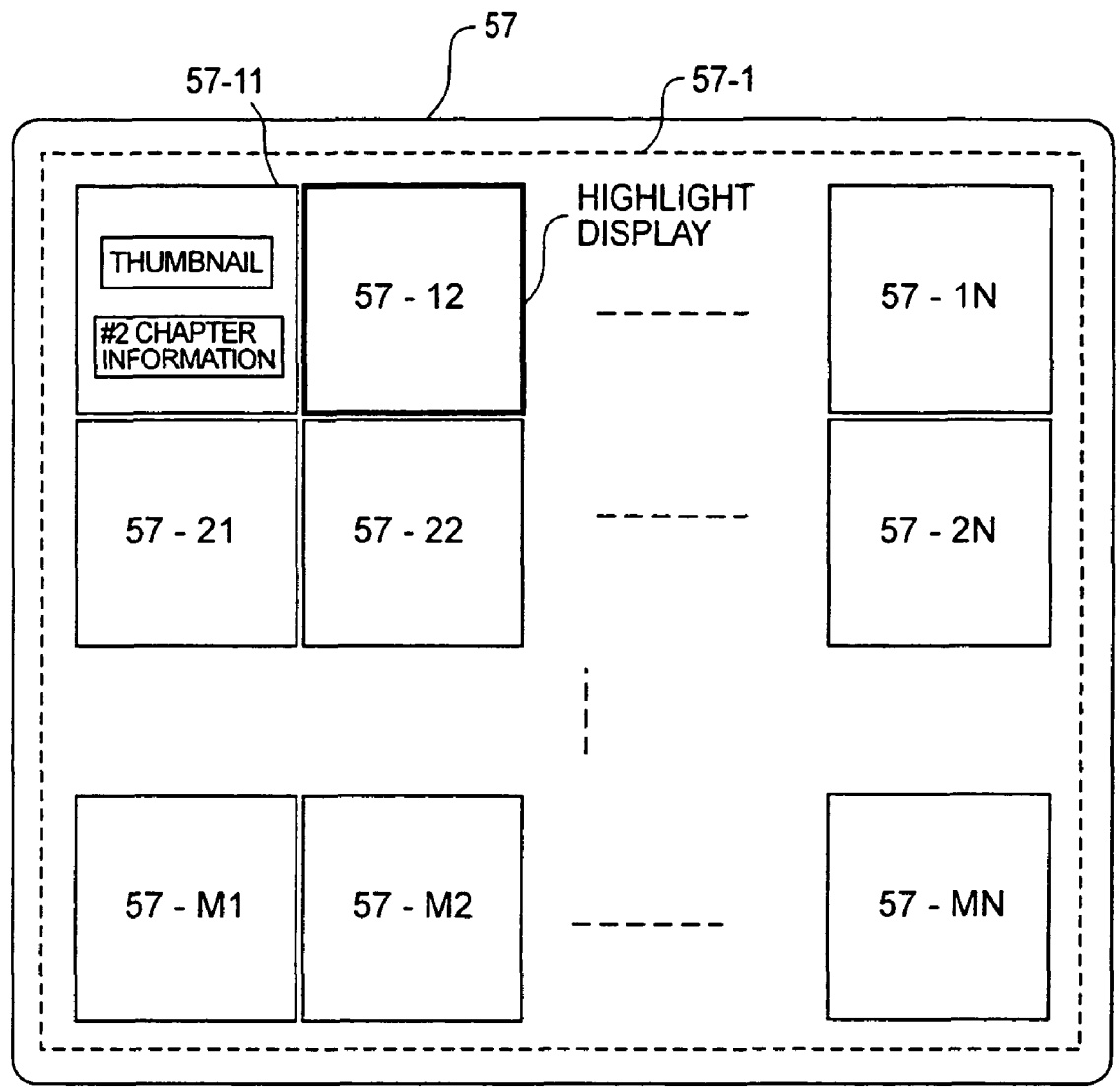
FIG. 10 is the second chapter index displayed on a monitor screen of the ultrasound diagnostic system in accordance with the first embodiment of the present invention.

FIG. 10 is an example of the second chapter index on a screen of monitor 5. Second chapter index screen 57 is provided with chapter display area displaying a predetermined disposition order of the second chapters to the number of N×M at maximum.

Each of the N×M second chapters is composed of thumbnail data and the second chapter information set up thereby in the same manner as shown in FIG. 9.

If image information memory 130 stores still or moving images in response to still or moving image storage operation of the recording operation of FIG. 2, for instance, provided through operation input device 6 at N×M times, index generator 140 makes a predetermined disposition order of second chapters 57-12 through 57-MN composed of the second chapter thumbnail data generated at such operation times and second chapter information and displays the same on chapter display area 57-1.

Since at this time the second chapter 57-11 corresponds to P examination image data, the second chapter 57-11 indicates recording start thumbnail data of P examination image data and the second chapter information set up from the second search information in response to an operation provided in advance through operation input device.

If still or moving image store operation time, examination items, image data generation modes, examinee ID, designation of still or moving images (image designation), moving image recording period of time, etc. are set up in advance as information displayed in the second chapter information, the second chapter 57-11 indicates still or moving image store operation time (recording start time) "T0", examination item of "abdomen", image data generation mode of "'B' mode image data", examinee ID of "79030310" and the like.

Further, the second chapter information of the second chapters 57-11 through 57-MN indicates, image designation of "still images" or "moving images", and moving image recording period of time of "5 seconds", if the moving images are designated, in addition to still or moving image store operation time, examination item, image data generation mode and the like.

The second chapter 57-12, for example, is highlighted in response to a highlight display moving operation provided through operation input device 6. Further, when a reproduction operation is instructed, index generator 140 switches a display to distinctive image data corresponding to the second chapter 57-12 and reproduces and display the same. When the distinctive image data are moving images, their reproduction and display are carried out at a predetermined reproduction rate.

When an image loop reproduction operation is provided through operation input device 6, index generator 140 reproduces distinctive image data corresponding to the second chapter from the highlighted second chapter in a predetermined order. When the distinctive image data are moving image data, their reproduction and display are carried out at the predetermined reproduction rate. When the distinctive image data are, however, still image data, distinctive image data of a next second chapter is displayed after their reproduction and display are carried out for a predetermined period of time. When the reproduction and display of one loop of the second chapter are terminated, the reproduction in response to the image loop reproduction operation ends.

Second chapter index screen 57 is not limited to a display for chapter display area 57-1 but may be provided for the second chapter display area to display a plurality of the second chapters and an image display area to display distinctive image data corresponding to the second chapter selectively displayed in the second chapter display area.

According to the medical image examination assistance system of the first embodiment, when distinctive operations are set up, examination image data are distinctively separated in accordance with a distinctive operation for on-going examinations and such separated examination image data can be incidental to search information based on the distinctive operation. Further, examination image data can be distinctively separated in response to a still or moving image store operation during the on-going examinations and the separated examination image data can be incidental to search information based on the distinctive operation. Thus, the operator can concentrate on examination.

When examination image data are inspected, all the examination lists stored in an image information memory can be displayed so that desired examination image data are easily searched, Further, since chapters including thumbnail or chapter information in the examination can be displayed and at the same time distinctive image data of a chapter can be reproduced and displayed, desired distinctive image data are easily located. Thus, this easy search for examination image data and distinctive image data can improve the efficiency of medical diagnosis.

The present invention is not limited to the first embodiment. Various modifications and changes to the same may be available. Image storage and examination device, for example, may be provided with a display module and a operation input module for the operation of the display module to display examination lists, and the first and second chapter indices and reproduce and display image data and the like.

When an image data generator outputs clear thumbnail data at a period of time t2 after the generation of a distinctive operation signal in response to a distinctive operation provided through an operation input device, the time at a period of time t2 after the generation of a distinctive operation signal may be regarded as distinctive time information.

Further, since distinctive image data are searched from the first chapter information, an ultrasound diagnostic system can use thumbnail data image that a data generator outputs not at time of distinctive time information but receipt time of an operation log ID when operation log ID discriminator 120 judges the operation log ID is proper.

Second Embodiment

Figure 11:
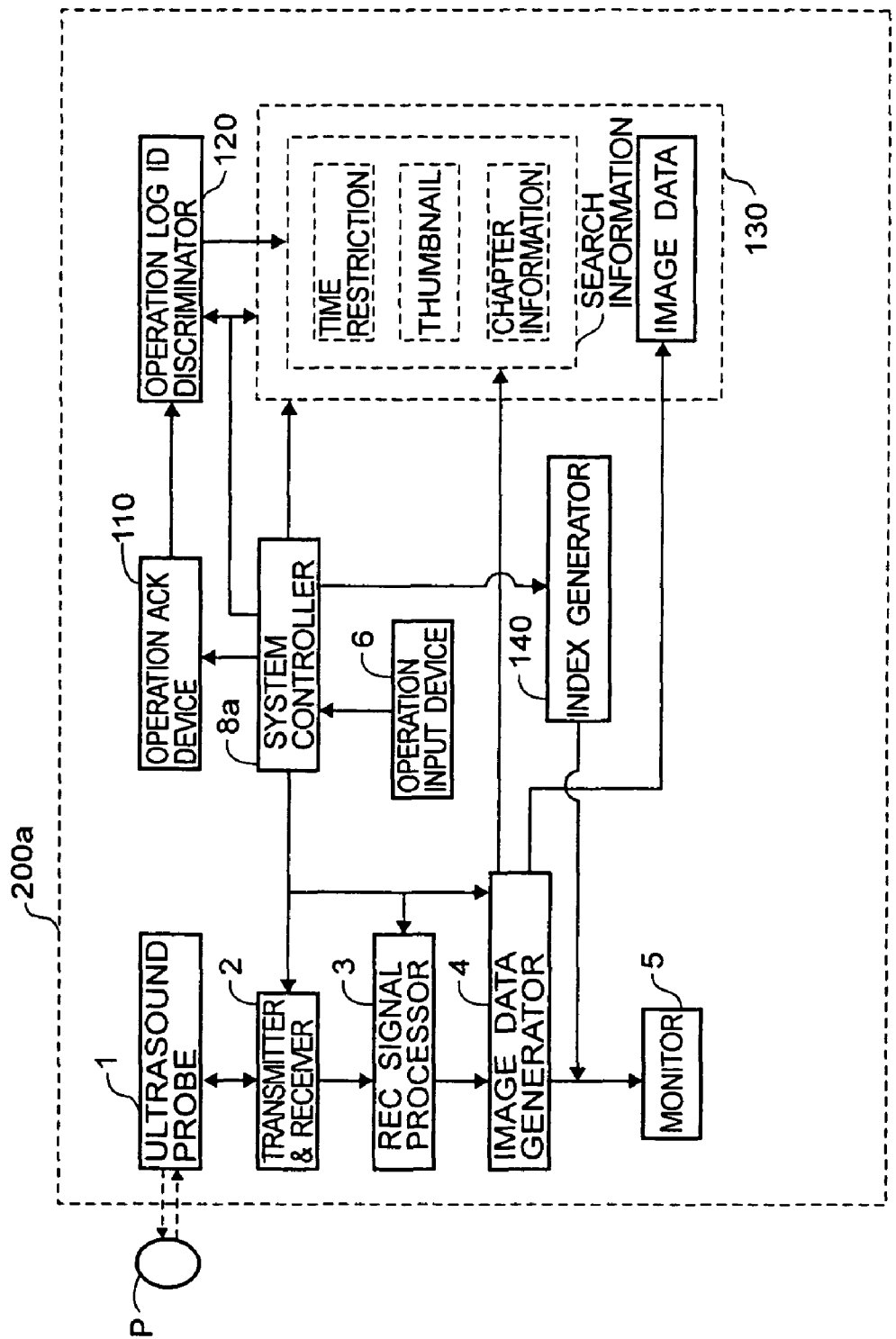
FIG. 11 is a block diagram of an ultrasound diagnostic system in accordance with the second embodiment of the present invention.

An ultrasound diagnostic system of the second embodiment in accordance with the present invention will be described below with reference to FIG. 11. The ultrasound diagnostic system of the second embodiment shown in FIG. 11 differs from the ultrasound diagnostic system of the embodiment shown in FIG. 1 in such structure that system controller 8 of ultrasound diagnostic device and controller 150 of image storage and perusal device 180 shown in FIG. 1 are replaced with system controller 8a of ultrasound diagnostic system 200a.

Ultrasound diagnostic system 200a is provided with system controller 8a which combines system controller 8 of ultrasound diagnostic device 10 and system controller 8 of image storage and perusal device 180 shown in FIG. 1 and has a structure similar to the one of ultrasound diagnostic system 200 from which interface 7 of ultrasound diagnostic device 10 and interface 100 of image storage and perusal device 180 are removed. Since operations of ultrasound diagnostic system 200a are the same as those of ultrasound diagnostic system 200 except those structural differences, their descriptions will be omitted.

According to ultrasound diagnostic system 200a of the second embodiment, when distinctive operations are set up, examination image data are distinctively separated in accordance with a distinctive operation for on-going examinations and such separated examination image data can be incidental to search information based on the distinctive operation. Further, examination image data can be distinctively separated in response to a still or moving image store operation during the on-going examinations and the separated examination image data can be incidental to search information based on the distinctive operation. Thus, the operator can concentrate on examination.

When examination image data are inspected, all the examination lists stored in an image information memory can be displayed so that desired examination image data are easily searched, Further, since chapters including thumbnail or chapter information in the examination can be displayed and at the same time distinctive image data of a chapter can be reproduced and displayed, desired distinctive image data are easily located. Thus, this easy search for examination image data and distinctive image data can improve the efficiency of medical diagnosis.

The present invention is not limited to the embodiments but may be subjected to various modifications without departing from the scope of the invention defined in the attached claims.

In the foregoing description, certain terms have been used for brevity, clearness and understanding, but no unnecessary limitations are to be implied therefrom beyond the requirements of the prior art, because such words are used for descriptive purposes herein and are intended to be broadly construed. Moreover, the embodiments of the improved construction illustrated and described herein are by way of example, and the scope of the invention is not limited to the exact details of construction. Having now described the invention, the construction, the operation and use of embodiments thereof, and the advantageous new and useful results obtained thereby; the new and useful construction, and reasonable equivalents thereof obvious to those skilled in the art, are set forth in the appended claims.

What is claimed is:

1. A medical image diagnostic apparatus for imaging an examinee for examination and for recording and reproducing obtained image data of a moving image, comprising:

an operation input device configured to input and set up operation items for performing during the imaging, the operation input device further setting up distinctive operation items of the moving image selected from the operation items, in advance of examination, the distinctive operation items including setting at least one of an examination item, an image data generation mode, and an image detector type;

a controller configured to cause a memory to store distinctive image data and corresponding thumbnail examination image data of the moving image being produced by each operation of the distinctive operation items, the controller further causing the memory to store search information being added to each of the distinctive image data of the moving image during the examination; and a monitor configured to display, by designating the search information corresponding to each of the distinctive operation items, each image of the thumbnail examination image data corresponding to the designated search information.

2. The medical image diagnostic apparatus according to claim 1, wherein the search information is added to a first frame of the distinctive image data.

3. The medical image diagnostic apparatus according to claim 1, wherein the images with the search information added are changed to the thumbnail examination image data and displayed.

4. The medical image diagnostic apparatus according to claim 1, wherein an information relative to time is added to the distinctive image data and stored in the memory, the information relative to time corresponding to operation input to the operation input device.

5. The medical image diagnostic apparatus according to claim 4, wherein the information relative to time is at a predetermined period of time after an operation signal is provided from the operation input device.

6. The medical image diagnostic apparatus according to claim 4, wherein the information relative to time is represented by a frame number of the distinctive image data.

7. The medical image diagnostic apparatus according to claim 1, wherein the distinctive operation item corresponds to an operation log ID.

8. The medical image diagnostic apparatus according to claim 7, further comprising an operation log ID discriminator, wherein the operation log ID is registered in advance, and the operation log ID discriminator judges whether the operation log ID corresponding to the operation input is consistent with the registered operation log ID.

9. The medical image diagnostic apparatus according to claim 7, wherein the operation log ID corresponds to image data generation modes and types of an image detector.

10. The medical image diagnostic apparatus according to claim 1, further comprising an index generator, wherein an information relative to examination is added to the image distinctive data and stored in the memory, and the index generator reads out the information relative to examination from the memory and prepares an index to make the monitor display the index.

11. A medical image diagnostic apparatus for imaging an examinee for examination and for recording and reproducing obtained image data of a moving image, comprising:
an interface circuit configured to receive inputs of operation items;
an operation input acknowledgement device configured to convert the inputs into operation log IDs;
an operation log ID discriminator configured to judge whether the operation log IDs are consistent with registered log IDs respectively and to issue each request for storing related information including information relative to time when each of the operation log IDs is provided to the operation input acknowledgement device, examinee ID at the time, examination information and thumbnail examination image data at the time during examination;
a controller configured to cause an image information memory to store distinctive examination image data of the moving image corresponding to each of the storing requests, the controller causing the image information memory to store the related information in association with the distinctive examination image data during the examination;
an image perusal controller configured to control reproducing the distinctive examination image data;
an index generator configured to receive a reproducing request from the image perusal controller and to generate a chapter index in accordance with the related information stored in the image information memory; and
a monitor configured to display each image of the thumbnail examination image data corresponding to each of the inputted operation items and to display the chapter index.

12. The medical image diagnostic apparatus according to claim 11, wherein the information relative to time is information at a predetermined period of time after an operation signal is provided from the operation input acknowledgement device.

13. The medical image diagnostic apparatus according to claim 11, wherein the information relative to time is represented by a frame number of the examination image data.

14. The medical image diagnostic apparatus according to claim 11, wherein the interface circuit registers log IDs corresponding to the operation log IDs, as the registered log IDs, in the operation log ID discriminator.

15. The medical image diagnostic apparatus according to claim 11, wherein the index generator reads out the examination information from the image information memory and makes the monitor display examination start time, examinee ID, and examination items.

16. The medical image diagnostic apparatus according to claim 11, wherein the index generator makes the monitor display each of the times when each of the operation log IDs is provided to the operation input acknowledgement device, the thumbnail examination image data, and the chapter index including the examination information.

17. The medical image diagnostic apparatus according to claim 11, wherein the operation log IDs correspond to image data generation modes and types of an image detector.

18. The medical image diagnostic apparatus according to claim 11, wherein the image information memory stores each of times when the examination image data, the thumbnail examination image data at the time, and the examination information associated with the examination image data at the time are respectively provided.

19. The medical image diagnostic apparatus according to claim 11, wherein the related information stored in the image information memory is associated with frame ID information, examination information in the frame ID information, and thumbnail examination image data of the distinctive examination image data.

20. The medical image diagnostic apparatus according to claim 1, wherein the search information includes information relative to time during the examination, examination information, and the thumbnail examination image data.

* * * * *